United States Patent
Yamamoto et al.

(10) Patent No.: US 6,215,031 B1
(45) Date of Patent: Apr. 10, 2001

(54) 3-HYDROXYMETHYLCYCLOALKANOLS AND PROCESS FOR PRODUCING THEM

(75) Inventors: Kenichi Yamamoto, Himeji; Kazuyuki Matsuoka, Nara; Hiroshi Yagihara, Himeji, all of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/155,242

(22) PCT Filed: Jan. 20, 1998

(86) PCT No.: PCT/JP98/00191
§ 371 Date: Sep. 24, 1998
§ 102(e) Date: Sep. 24, 1998

(87) PCT Pub. No.: WO98/32723
PCT Pub. Date: Jul. 30, 1998

(30) Foreign Application Priority Data

Jan. 24, 1997 (JP) .................................... 9-011066

(51) Int. Cl.[7] .................................... C07C 31/13
(52) U.S. Cl. .................... 568/831; 568/821; 568/822; 568/835; 568/832
(58) Field of Search .................... 568/821, 822, 568/831, 832, 833, 835, 836, 838

(56) References Cited

U.S. PATENT DOCUMENTS 5,532,372 * 7/1996 Saji et al. .................... 544/368

FOREIGN PATENT DOCUMENTS 58-154528 * 9/1983 (JP) .

OTHER PUBLICATIONS

Harrison et al; Compendium of Organic Synthetic Methods, pp. 82–84 and 112–118, 1971.*
Database Crossfire Online, Beilstein Informationssysteme Gmbh, Frankfurt DE, XP002119457, Jun. 29, 1989.
Database Crossfire Online, Beilstein Informationssysteme Gmbh, Frankfurt DE, XP002119458, Jun. 29, 1989.
Database Crossfire Online, Beilstein Informationssysteme Gmbh, Frankfurt DE, XP002119459, Jul. 5, 1989.
Database Crossfire Online, Beilstein Informationssysteme Gmbh, Frankfurt DE, XP002119460, Oct. 20, 1993.
Database Crossfire Online, Beilstein Informationssysteme Gmbh, Frankfurt DE, XP002119461, Jun. 29, 1989.
Database Crossfire Online, Beilstein Informationssysteme Gmbh, Frankfurt DE, XP002119462, Apr. 18, 1994.
Database Crossfire Online, Beilstein Informationssysteme Gmbh, Frankfurt DE, XP002119463, Nov. 8, 1994.
Database Crossfire Online, Beilstein Informationssysteme Gmbh, Frankfurt DE, XP002119464, Feb. 15, 1990.
Database Crossfire Online, Beilstein Informationssysteme Gmbh, Frankfurt DE, XP002119465, Feb. 3, 1995.
Database Crossfire Online, Beilstein Informationssysteme Gmbh, Frankfurt DE, XP002119466, Apr. 18, 1994.
Patent Abstracts of Japan, vol. 1998, No. 11 (Sep. 30, 1998).
Mercury (II)–Mediated Opening of Cyclopropanes. Effects of Proximate Internal Nucleophiles on Stero–and Regioselectivity, Journal of the American Chemical Society, J. Am. Chem. Soc. 1983, 105, 6882–6889.
Biotransformation of (–)–and (+)–Neomethols and Isomentol by *Aspergillus niger*, 0031–9422 (93)E)) ()–2, Phytochemistry, vol. 33, No., 6, pp. 1465–1467 (1994).
Zerfall von 2–Oxa–5–und–6–norbornadiazonium–Ionen, Wolfgang Kirmse un Uwe Mrotzeck, Sep. 21, 1987, Chem. Ber. 121 485–492 (1988) VCH Verlagsgesellshaft mbh. D–6940, pp. 485–492.

\* cited by examiner

Primary Examiner—Sreeni Padmanabhan
(74) Attorney, Agent, or Firm—Birch, Stewart, Kolasch & Birch, LLP

(57) ABSTRACT

The present invention relates to a 3-hydroxymethylcycloalkanol of the following formula (1), and a process for production of a 3-hydroxymethylcycloalkanol of the formula (1) by reduction of 3-formylcycloalkanone or 3-formylcycloalkenone.

In accordance with the present invention, 3-hydroxymethylcycloalkanol, which is useful as the starting material for the production of polymers, can be produced with high conversion and high selectivity.

(1)

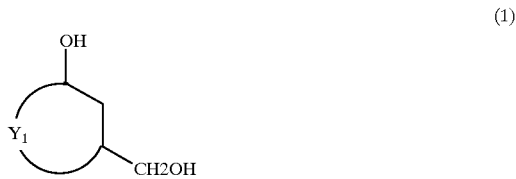

11 Claims, No Drawings

3-HYDROXYMETHYLCYCLOALKANOLS AND PROCESS FOR PRODUCING THEM

This application is the national phase under 35 U.S.C. §371 of prior PCT International Application No. PCT/JP98/00191 which has an International filing date of Jan. 20, 1998 which designated the United States of America, the entire contents of which are hereby incorporated by reference.

TECHNICAL FIELD

The present invention relates to a 3-hydroxymethylcycloalkanol which is useful as, for example, polyhydric alcohol component of thermoplastic and thermosetting polymers and to a process for producing the same.

BACKGROUND TECHNOLOGY

With the expanding application of polyester and polyurethane in recent years, there exists a demand for improvements in various polymer properties including weather resistance, water resistance, heat resistance, resistance to chemicals, electrical characteristics, and mechanical characteristics. In order to improve those polymer properties, there exist many researches for polyhydric alcohols which are component of those polymer. As the polyhydric alcohol, it is known that aliphatic polyols such as ethylene glycol, diethylene glycol, propylene glycol, butylene glycol, hexanetriol, trimethylolpropane, pentaerythritol and alicyclic diols such as 1,3-cyclohexanedimethanol, 1,4-cyclohexanedimethanol.

However, with those polyhydric alcohols, all the above-mentioned prperties can hardly be implemented in a well-assorted balance.

It is, therefore, an object of the present invention to provide a polyhydric alcohol useful as the starting material in the production of the polymers and a process for producing the polyhydric alcohol.

It is another object to provide a technology for providing the polyhydric alcohol efficiently.

DISCLOSURE OF INVENTION

Having explored into the art for accomplishing the above objects, the inventors of the present invention found that 3-hydroxymethylcycloalkanols are useful as the starting material in the production of the polymers.

Thus, an 3-hydroxymethylcycloalkanol of the present invention is a compound of the following formula (1).

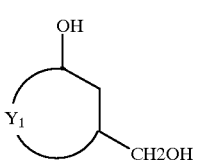

(1)

wherein $Y_1$ represents a saturated aliphatic hydrocarbon group. This 3-hydroxymethylcycloalkanol can be produced by reduction of a 3-formylcycloalkanone or a 3-formylcycloalkenone.

BEST MODE FOR CARRYING OUT THE INVENTION

3-Hydroxymethylcycloalkanol

Referring to any 3-hydroxymethylcycloalkanol of the above formula (1), the bivalent saturated aliphatic hydrocarbon group designated by $Y_1$ may be straight-chain or branched, and, in the case of a branched-chain hydrocarbon group, the same carbon atom may be substituted by 1 or 2 alkyl groups. The aliphatic hydrocarbon group includes, for example, $C_{1-10}$ alkylene groups such as methylene, ethylene, propylene, trimethylene, 2-methyltrimethylene, 2,2-dimethyltrimethylene, tetramethylene, 2-methyltetramethylene, 2,2-dimetyhltetramethylene, pentamethylene, hexamethylene, and so forth. Preferred straight-chain and branched alkylene groups are $C_{2-8}$ alkylene groups, with $C_{2-6}$ alkylene groups being particularly preferred.

Those aliphatic hydrocarbon groups may each be substituted, in suitable positions, by various substituent groups, for example, hydroxyl, $C_{1-4}$ alkoxy, carboxy, alkoxycarbonyl, alicyclic hydrocarbon groups (cycloalkyl, cycloalkenyl, cycloalkinyl groups, etc.), and aromatic hydrocarbon groups (aryl groups such as phenyl group).

The 3-hydroxymethylcycloalkanol of the above formula (1) includes, for example, 3-hydroxymethylcyclopentanol, 3-hydroxymethylcyclohexanol, 3-hydroxymethyl-5-methylcyclohexanol, 3-hydroxymethylcycloheptanol, 3-hydroxymethyl-5,5-dimethylcyclohexanol, 3-hydroxymethylcyclooctanol, 3-hydroxymethyl-5-methylcyclooctanol, 5-phenyl-3-hydroxymethylcyclohexanol, and so forth. The preferred 3-hydroxymethylcycloalkanol is 3-hydroxymethyl-5,5-dimethylcyclohexanol.

When such an 3-hydroxymethylcycloalkanol is used as a starting material in the production of polymers (e.g. diol component of polyesters or polyurethanes, polyhydric alcohol component of epoxy resin), polymers with excellent weather resistance, inhibition the decrease of mechanical strength, and good resistance to chemicals can be obtained due to the existence of substituted hydroxy groups on the alicyclic skeleton and on the methyl group. Moreover, because a cyclic structure is introduced, polymers with high melting points and improved heat resistance can be obtained. In addition, because of its alicyclic structure, polymers of low polarity, good water resistance, and excellent electrical characteristics can be obtained.

Process for Producing a 3-Hydroxymethylcycloalkanol

As illustrated in the following reaction process scheme, the process of the present invention comprises subjecting a 3-formylcycloalkanone or 3-formylcycloalkenone of the following formula (2) (hereinafter may refferd to briefly as the substrate compound) to catalytic reduction in the presence of a catalyst to give a 3-hydroxymethylcycloalkanol of the following formula (1). The substrate 3-formylcycloalkanone or 3-formylcycloalkenone of the formula (2) can be obtained by various methods, for example, by oxidizing a 3-methylcycloalkanone or 3-methylcycloalkenone of the following formula (3). The 3-methylcycloalkenones, as the starting material, are easily produced by condensation of acetones, and 3-methyl-2-cyclopenten-1-on is easily produced by isomerization of 2-cyclohexen-1-on.

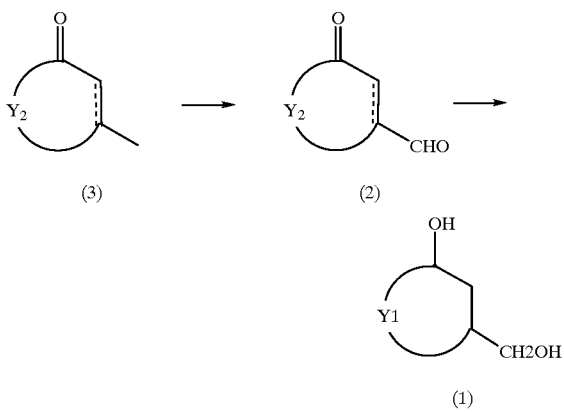

wherein $Y_1$ represents a saturated aliphatic hydrocarbon group; $Y_2$ represents a saturated or unsaturated hydrocarbon group.

Process for Producing Compound (2)

The 3-formylcycloalkanone or 3-formylcycloalkenone of the above formula (2) may be produced by oxidation of the 3-methylcycloalkanone or 3-methylcycloalkenone of the above formula (3). The 3-formylcycloalkenone or 3-formylcycloalkanone can be produced by an oxidation reaction with oxygen in the presence of a catalyst such as a metal oxide (selenium oxide, chromium oxide, dichromic acid, and oxides of copper, silver, lead, etc.), a naphthenic acid salt (cobalt, chromium, or other salt), or a vanadium oxide catalyst ($V_2O_5$—$SnO_2$, $V_2O_5$—$SnO_2$—$Fe_2O_3$, $V_2O_5$—$Fe_2O_3$, etc.), an oxidation reaction with oxygen, as described in Japanese Patent Application Laid-open No.154528/1983 (JP-A-58-154528), in the presence of at least one metal salt selected from the group consisting of salts of iron, ruthenium, rhodium, cobalt, etc., or an oxidation process using a heteropolyacid or a salt thereof as the catalyst. Preferred is the process for producing a 3-formylcycloalkenone by using a 3-methylcycloalkenone in combination with, as the oxidation catalyst, a heteropolyacid or a salt thereof.

The heteropolyacid is an oxy-acid condensate containing 2 or more dissimilar center ions and is also known as a heteronuclear condensed acid. The heteropolyacid may for example be composed of the oxy-acid ion (e.g. phosphate, silicate, etc.) of an element such as P, As, Sn, Si, Ti, or Zr and the oxy-acid (e.g. vanadic acid, molybdic acid, tungstic acid, etc.) of an element such as V, Mo, or W. A variety of heteropolyacids for use as catalysts can be obtained according to various combinations of such oxy-acid ion and oxy-acid.

The preferred heteropolyacid anion can be expressed by $XM_{12}O_{40}$. "X" represents an element such as Si, P, or the like and "M" represents an element such as Mo, W, V, or the like. The heteropolyacid having such a composition includes phosphomolybdic acid, phosphotungstic acid, silicomolybdic acid, silicotungstic acid, phosphovanadomolybdic acid, and so forth. The preferred heteropolyacid are phosphomolybdic acid and phosphovanadomolybdic acid, with phosphovanadomolybdic acid being particularly preferred.

Phosphovanadomolybdic acid or its salt is expressed by the following formula.

$$A_{3+n}[PV_nMo_{12-n}O_{40}]$$

wherein "A" represents a heteropolyacid cation and n represents an integer of 1 to 10.

The heteropolyacid cation designated by "A" need not only be hydrogen atom but also may be a cation other than H, for example $NH_4$, an alkali metal (e.g. Cs, Rb, K, Na, Li) cation or an alkaline earth metal (e.g. Ba, Sr, Ca, Mg) cation.

While the heteropolyacid as a free heteropolyacid is sufficiently active, at least some of the hydrogen cation atoms as counter cation of the heteropolyacid may be replaced with a different cation. By such partial substitution of the heteropolyacid, the heteropolyacid can be insolubilized to enhance its stability and heat resistance, thus providing the more useful catalyst. The species of substituent cation that can be used is not particularly restricted but includes $NH_4$, alkali metals (Cs, Rb, K, Na, Li, etc.) cation and alkaline earth metals (e.g. Ba, Sr, Ca, Mg) cation, and so forth. Particularly when the heteropolyacid is partially substituted by ammonium cations to make a mixed cation composition of H and $NH_4$, the catalyst activity and stability are still more improved. In this connection, the molar ratio of $NH_4$ to H may be $NH_4/H$=about 0.1 to 10, preferably $NH_4/H$=about 0.2 to 8, and more preferably $NH_4/H$=about 0.3 to 5.

The value of "n" can be judiciously selected in consideration of oxidizing ability and stability, and may for example be about 1 to 10, preferably about 4 to 10 (for example 4 to 8), and more preferably about 5 to 8. When the counter cation moiety of the heteropolyacid is constituted by H and a cation other than H (for example $NH_4$), the value of "n" maybe about 4 to 10 in many instances. Such heteropolyacids inclusive of their salts can be used each alone or in combination.

The heteropolyacid inclusive of its salt can be used as it is as a catalyst but may be used in the form of a supported catalyst or solid catalyst as immobilized on a suitable supports. The catalyst activity of the heteropolyacid is increased when it is so immobilized.

The support or carrier which can be used for immobilizing the catalyst substance includes the conventional support or carrier materials inclusive of inorganic supports such as activated carbon, alumina, silica, silicon carbide, silica-alumina, bentonite, magnesia, titania, vanadia, zirconia, zeolite, diatomaceous earth, kaolin, etc. and organic supports such as styrene-divinylbenzene copolymer. The preferred support includes porous supports such as activated carbon, alumina, titania, silicon carbide, silica-alumina, bentonite, and zeolite, and so on. Particularly preferred is activated carbon. When activated carbon is used, the selectivity for oxidation of the 3-methyl group of the substrate compound can be still more improved. Activated carbon may be particulate or fibrous.

The specific surface area of the support is not particularly restricted but may for example be about 10 to 4500 $m^2/g$, preferably about 50 to 4000 $m^2/g$, and usually about 100 to 3000 $m^2/g$. For enhanced catalyst activity, the preferred specific surface area of activated carbon may for example be about 300 to 4000 $m^2/g$, preferably about 400 to 3000 $m^2/g$. In many instances, activated carbon with a specific surface area of about 500 to 2000 $m^2/g$ is selected.

The mean pore diameter of activated carbon may be about 5 to 200 Angstrom units, preferably about 10 to 100 Angstrom units. The pore volume of activated carbon may for example be about 0.1 to 10 ml/g, preferably about 0.3 to 5 ml/g.

The amount of the heteropolyacid inclusive of its salt relative to the support can be freely selected within the range not detracting from catalyst activity and, based on 100 parts by weight of the support, may for example be about 0.1 to 100 parts by weight, preferably about 0.5 to 50 parts by weight, more preferably about 5 to 30 parts by weight, and, for still better results, about 5 to 20 parts by weight.

Immobilization of the heteropolyacid inclusive of its salt on such a support can be effected by the conventional technology, for example immersion, coating, spray-coating, adsorption, or precipitation. Particularly, a procedure capable of supporting the catalyst component uniformly in a highly dispersed state on the support, for example an immersion process or an adsorption process, can be used with advantage.

In immobilizing the heteropolyacid or its salt, it is common practice to use a solvent such as water and cause a solution of the catalyst component in such a solvent to be uniformly supported.

The amount of the heteropolyacid or its salt is dependent on its species but is usually selected from the range of 0.1 to 50 weight % in terms of the heteropolyacid or salt relative to 3-methylcycloalkanone or 3-methylcycloalkenone.

In the practice of the present invention, not only oxygen or an oxygen-containing gas but also compounds capable of liberating oxygen can be used as the oxygen source. The oxygen source may for example be oxygen gas of high purity. Where necessary, the oxygen gas may be diluted with an inert gas such as nitrogen, helium, argon, or carbon dioxide gas, and the diluted oxygen gas may be fed to the reaction system. When an inert gas is used as a diluent gas, it is possible to use air in lieu of oxygen so that the nitrogen in the air may serve as the inert gas.

The concentration of oxygen per mole of the substrate compound may be 0.5 mole or more (0.5 to 1000 moles), preferably a stoichiometric excess (1 to 1000 moles). The reaction is usually carried out in the presence of a large excess of oxygen, for example in an oxygen atmosphere or an oxygen-containing gas atmosphere.

The oxidation reaction may be whichever of gas-phase oxidation and liquid-phase oxidation. The reaction can be conducted in the absence of a solvent or in the presence of an inert solvent indifferent to the reaction. The solvent mentioned just above includes aromatic hydrocarbons such as benzene, toluene, xylene, ethylbenzene, etc.; aliphatic hydrocarbons such as hexane, heptane, octane, etc.; alicyclic hydrocarbons such as cyclohexane etc.; halogenated hydrocarbons such as carbon tetrachloride, chloroform, dichloromethane, 1,2-dichloroethane, etc.; carboxylic acids such as acetic acid, propionic acid, butyric acid, etc.; ketones such as acetone, methyl ethyl ketone, etc.; esters such as methyl acetate, ethyl acetate, isopropyl acetate, butyl acetate, etc.; ethers such as diethyl ether, dibutyl ether, dimethoxyethane, dioxane, tetrahydrofuran, etc.; amides such as N,N-dimethylformamide, N,N-dimethylacetamide, etc.; and nitriles such as acetonitrile, propionitrile, benzonitrile, and so forth. Those solvents can be used each alone or in combination.

The reaction temperature can be freely selected according to the desired reaction rate and selectivity and may for example be about 30 to 300° C., preferably about 50 to 200° C.

Substrate Compound

The 3-formylcycloalkanone or 3-formylcycloalkenone of the formula (2), which is used as the substrate compound, is a cyclic ketone having a formyl group in the β-position and includes 3-formylcycloalkanones such as 3-formylcyclopentanone, 3-formylcyclohexanone, 5-methyl-3-formylcyclohexanone, 3-formylcycloheptanone, 5,5-dimethyl-3-formylcyclohexanone, 3-formylcyclooctanone, 5-methyl-3-formylcyclooctanone, 5-phenyl-3-formylcyclohexanone, etc. and 3-formylcycloalkenones such as 3-formylcyclopentenone, 3-formylcyclohexenone, 5-methyl-3-formylcyclohexenone, 3-formylcycloheptenone, 5,5-dimethyl-3-formylcyclohexenone, 3-formylcyclooctenone, 5-methyl-3-formylcyclooctenone, 5-phenyl-3-formylcyclohexenone, and so forth. Only provided that the above basic structural feature is retained, bicyclic fused compounds sharing two or more carbon atoms (for example 4-formylbicyclo[4.4.0]decan-3-en-2-one) may also be used.

Reduction Reaction

The reduction reaction for converting a compund of the formula (2) to compound of the formula (1) can be carried out by the catalytic reduction method using hydrogen in the presence of a catalyst.

The catalyst which can be used for this reduction reaction (hereinafter may referred to as catalyst component) includes many kinds of catalysts for catalytic reduction such as nickel compounds (reducing nickel, Raney nickel, etc.), cobalt compounds (cobalt, Raney cobalt, etc.), platinum compounds (platinum black, platinum oxide, etc.), palladium compounds (palladium, palladium black, etc.), rhodium, ruthenium, copper chromite, copper-chromium catalyst, and so forth. In order to reduce the oxo group, many kinds of metal hydride are used such as $LiAlH_4$, $LiAlH(OR)_3$ (wherein R represents $C_{1-4}$ alkyl group such as methyl or ethyl group), $AlH_3$, $BH_3$, $NaBH_4$, $LiBHEt_3$ (wherein Et represents ethyl group), and so on. Moreover, the above catalysts for the catalytic reduction can be used after the reduction of the oxo group by the above metal hydride.

The above catalyst can be used as it is but may be used as a supported catalyst or solid catalyst as immobilized on a support.

The support or carrier which can be used for supporting the above catalyst component includes the conventional support or carrier materials inclusive of inorganic supports such as activated carbon, carbon black, alumina, silica, silicon carbide, silica-alumina, bentonite, magnesia, titania, vanadia, zirconia, zeolite, diatomaceous earth, kaolin, barium sulfate, etc. and organic supports such as styrene-divinylbenzene copolymer. The preferred support includes porous supports such as activated carbon, alumina, carbon black, silicon carbide, silica-alumina, bentonite, zeolite, and barium sulfate.

The specific surface area of the support is not particularly restricted but may for example be about 0.1 to 4500 $m^2/g$, preferably about 0.5 to 4000 $m^2/g$, and usually about 1 to 2000 $m^2/g$.

The amount of the catalyst relative to the support can be selected within the range contributory to enhanced catalyst activity and may for example be about 0.1 to 100 parts by weight, preferably about 0.5 to 50 parts by weight, more preferably about 5 to 30 parts by weight, and, particularly, 5 to 20 parts by weight, based on 100 parts by weight of the support.

Immobilization of the catalyst on the support or carrier can be effected by the conventional technology, for example immersion, coating, spray-coating, adsorption, or precipitation. Particularly, a procedure capable of supporting the catalyst component uniformly in a highly dispersed state on the support, for example an immersion process or an adsorption process, can be used with advantage.

The amount of the catalyst depends on its species but is generally selected from the range of 0.1 to 50 weight %, as catalyst component, relative to the substrate compound.

The hydrogen source for use in the catalytic reduction reaction according to the present invention includes hydrogen and a hydrogen-containing gas. As such a hydrogen source, hydrogen gas of high purity can be used, and, where necessary, hydrogen gas diluted with an inert gas indifferent to the reaction, such as nitrogen, helium, or argon gas, may be fed to the reaction system.

The hydrogen pressure is usually selected within the range of about 1 to 250 $kgf/cm^2$, preferably about 2 to 200 $kgf/cm^2$, and more preferably about 10 to 150 $kgf/cm^2$.

The reduction reaction can be carried out in the absence of a solvent or in an inert solvent. The solvent which can be used for this reduction reaction includes aliphatic hydrocarbons such as hexane, heptane, octane, etc.; alicyclic hydrocarbons such as cyclohexane, etc.; alcohols such as methanol, ethanol, isopropanol, butanol, ethyleneglycol, diethyleneglycol, 1,4-butanediol, cyclohexanol, etc.; esters such as methyl acetate, ethyl acetate, isopropyl acetate, butyl acetate, etc.; amides such as N,N-dimethylformamide, N,N-dimethylacetamide, etc.; ethers such as diethyl ether, dibutyl ether, dimethoxyethane, dioxane, tetrahydrofuran, ethylene glycol monomethyl ether, diethylene glycol dimethyl ether, 1-methoxy-2-prpanol, etc.; and so forth. The solvent which is usually employed includes alcohols and ethers. Those solvents can be used each alone or in combination.

The proportion of the solvent relative to 1 part by weight of 3-formylcycloalkanone or 3-formylcycloalkenone is about 1 to 100 parts by weight, preferably about 3 to 50 parts by weight, and more preferably about 5 to 30 parts by weight.

The reaction temperature can be judiciously selected with reference to reaction kinetics and selectivity and may for example be about 30 to 250° C., preferably about 50 to 230° C., and more preferably about 100 to 200° C.

This reaction can be carried out with stirring in accordance with conventional technology. The reaction product 3-hydroxymethylcycloalkanol can be easily isolated and purified by the conventional separation procedure such as filtration, concentration, distillation, extraction, crystallization, recrystallization, or column chromatography, or a combination of such procedures.

INDUSTRIAL APPLICABILITY

The resulting 3-hydroxymethylcycloalkanol of the present invention finds application as a reagent, an intermediate of drugs and perfumes, a compound for the production of polymers for which a polyhydric alcohol is used as a starting material, such as thermosetting polymers (e.g. unsaturated polyesters, polyurethanes, epoxy resins) and thermoplastic polymers (e.g. saturated polyesters, thermoplastic polyurethanes, polycarbonates). these resins are useful for coating materials, synthetic fibers, and resins for molding products.

The unsaturated polyesters are synthesized by condensation of dicarboxylic component containing unsaturated dibasic acids such as maleic anhydride and diol component containing at least 3-hydroxymethylcycloalkanol. The polyurethanes or the thermoplastic polyurethanes are produced by the reaction of polyisocyanates such as tolylenediisocyanate and diol component containing at least 3-hydroxymethylcycloalkanol. The epoxy resins are produced by the reaction of the 3-hydroxymethylcycloalkanol and epichlorohydrin. The saturated polyesters are produced by polycondensation of saturated dibasic acids such as terephthalic acid and adipic acid, and diol component containing at least 3-hydroxymethylcycloalkanol. The polycarbonates are produced by the reaction of diol component containing at least 3-haydroxymethylcycloalkanol and carbonates such as phosgene and diphenylcarbonate.

In accordance with the present invention, 3-hydroxymethylcycloalkanols, one member of polyhydric alcohols, useful as the starting material for the production of polymers can be provided. Moreover, such 3-hydoroxymethylcycloalkanols can be produced with high efficiency.

EXAMPLES

The following examples illustrate the present invention in further detail, it being to be understood, however, that these examples should by no means be construed as defining the scope of the invention.

Example 1

To 43.90 g of sodium metavanadate and 49.32 g of sodium molybdate was added 300 ml of water and the mixture was heated at 95° C. to prepare a solution. To this solution, a solution prepared from 45.6 g of 85% phosphoric acid and 60 ml of water was added, and the mixture was kept at 95° C. for 1 hour, with constant stirring. The mixture was then cooled to 0° C. and a solution of 35.6 g of ammonium chloride in 126 ml of water was added. Whereupon a brown precipitate separated out. The precipitate was collected by filtration and recrystallized twice from water to provide a heteropolyacid ammonium salt. Analysis of this heteropolyacid ammonium salt was $(NH_4)_5H_6[PV_8Mo_4O_{40}] \cdot 9.6H_2O$.

To a solution prepared from 200 mg of the above heteropolyacid ammonium salt and 4000 ml of water was added 1800 mg of activated carbon, and the mixture was stirred for 1 hour and then allowed to stand at room temperature. It was then filtered and the cake was washed with 4000 ml of water and dried at 80° C. to provide a catalyst supported on the carbon.

A glass flask (capacity 50 ml) was charged with 1.75 g of the above catalyst, 1.38 g of isophorone, and 20 g of toluene and the reaction was carried out under oxygen atmosphere at the reflux temperature for 20 hours. Analysis of this reaction mixture by gas chromatography revealed that 93% of isophorone had reacted, with 62% of the reacted isophorone having been converted to 5,5-dimethyl-3-formylcyclohexanone (yield 58 weight %).

An autoclave (capacity 300 ml) equipped with an electromagnetic stirrer was charged with the 5 g of the above 5,5-dimethyl-3-formylcyclohexanone, 100 g of methanol, and 1 g of Raney nickel. After the temperature was increased to 180° C., the reaction was carried out under a hydrogen partial pressure of 70 kgf/cm$^2$ at a stirring speed of 800 to 1000 rpm for 2 hours.

After completion of the reaction, the autoclave was cooled and relieved of pressure and the reaction mixture was withdrawn. The catalyst was then filtered off and the methanol was evaporated off at atmospheric pressure, whereby 4.4 g of a substance was obtained. Of this substance, 3-hydroxymethyl-5,5-dimethylcyclohexanol accounted for 96.9% by weight. This substance was analyzed by mass spectrometry and elemental analysis.

Mass Spectrum

MS molecular ion peaks (m/e): 158 (theoretical molecular mass 158), 141, 140, 128, 127, and 57.

Elemental Analysis (for $C_9O_2H_{18}$)

|  | C | O | H |
| --- | --- | --- | --- |
| Found: | 68.1; | 9.9; | 22.0 |
| Calcd.: | 68.4; | 10.1; | 20.3 |

Example 2

A heteropolyacid ammonium salt of the composition $(NH_4)_3H_6[PV_8M_4O_{40}]$ was immobilized or supported on activated carbon as in Example 1. Using this catalyst-on-carbon, the reaction was carried out in the same manner as in Example 1. As a result, 94% of isophorone reacted and 60% of the reacted isophorone was converted to 5,5-dimethyl-3-formylcyclohexanone (yield 56 weight %).

This 5,5-dimethyl-3-formylcyclohexanone was subjected to the same reduction reaction as in Example 1 to provide 3-hydroxymethyl-5,5-dimethylcyclohexanol as in Example 1.

Example 3

A heteropolyacid ammonium salt of the composition $(NH_4)_4H_4[PV_5Mo_7O_{40}]$ was immobilized or supported on activated carbon as in Example 1. Using this catalyst-on-carbon, the reaction was conducted in the same manner as in Example 1. As a result, 83% of isophorone reacted and 60% of the reacted isophorone was converted to 5,5-dimethyl-3-formylcyclohexanone (yield 50 weight %).

When this 5,5-dimethyl-3-formylcyclohexanone was subjected to reduction reaction in the same manner as in Example 1, 3-hydroxymethyl-5,5-dimethylcyclohexanol was obtained as in Example 1.

Example 4

A heteropolyacid ammonium salt of the composition $(NH_4)_3H_4[PV_4Mo_8O_{40}]$ was immobilized or supported on activated carbon in the same manner as in Example 1. Using this catalyst-on-carbon, the reaction was carried out in the same manner as in Example 1. As a result, 79% of isophorone reacted and 61% of the reacted isophorone was converted to 5,5-dimethyl-3-formylcyclohexanone (yield 48 weight %).

When the above 5,5-dimethyl-3-formylcyclohexanone was subjected to reducton reaction as in Example 1, 3-hydroxymethyl-5,5-dimethylcyclohexanol was obtained as in Example 1.

It will be apparent from the above examples, the novel 3-hydroxymethyl-5,5-dimethylcyclohexanol can thus be obtained. Moreover, by the process of the present invention, 3-hydroxymethyl-5,5-dimethylcyclohexanol can be produced with high conversion and high selectivity.

What is claimed is:
1. A 3-hydroxymethylcycloalkanol which is a 3-hydroxymethyl-5,5-dimethylcyclohexanol.
2. A process for producing 3-hydroxymethylcycloalkanol of the following formula (1)

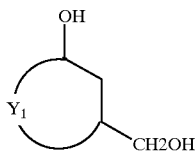

(1)

wherein $Y_1$ represents a saturated aliphatic hydrocarbon group, which comprises subjecting a 3-formylcycloalkanone or 3-formylcycloalkenone of the following formula (2) to reduction

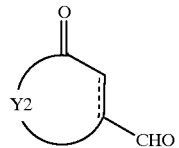

(2)

wherein $Y_2$ represents a saturated or unsaturated aliphatic hydrocarbon group.
3. A 3-hydroxymethylcycloalkanol, which is a 3-hydroxymethyl-5-methylcyclooctanol.
4. A 3-hydroxymethylcycloalkanol, which is a 5-phenyl-3-hydroxymethylcyclohexanol.
5. A process for producing 3-hydroxymethylcycloalkanol of the following formula (1)

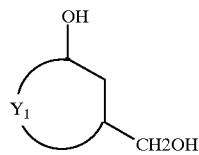

(1)

wherein $Y_1$ represents a saturated aliphatic hydrocarbon group, which comprises oxidizing a 3-methylcycloalkanone or 3-methylcycloalkenone to produce a 3-formylcycloalkanone or 3-formylcycloalkenone of the following formula (2)

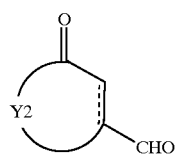

(2)

wherein $Y_2$ represents a saturated or unsaturated aliphatic hydrocarbon group, and reducing the 3-formylcycloalkanone or 3-formylcycloalkenone.
6. The process according to claim 2, wherein the 3-hydroxymethylcycloalkanol is a 3-hydroxymethylcyclohexanol.
7. The process according to claim 2, wherein 3-hydroxymethylcycloalkanol is a 3-hydroxymethyl-5-methylcyclohexanol.
8. The process according to claim 2, wherein 3-hydroxymethylcycloalkanol is a 3-hydroxymethylcycloheptanol.
9. The process according to claim 2, wherein 3-hydroxymethylcycloalkanol is a 3-hydroxymethylcyclooctanol.
10. The process according to claim 2, wherein 3-hydroxymethylcycloalkanol is a 3-hydroxymethyl-5-methylcyclooctanol.
11. The process according to claim 2, wherein 3-hydroxymethylcycloalkanol is a 5-phenyl-3-hydroxymethylcyclohexanol.

* * * * *